(12) United States Patent
Allen

(10) Patent No.: US 9,277,967 B2
(45) Date of Patent: Mar. 8, 2016

(54) UNIVERSALLY-SIZED GROMMET DEVICE AND METHOD THEREOF

(75) Inventor: Kraig Herman Allen, Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 585 days.

(21) Appl. No.: 13/614,171

(22) Filed: Sep. 13, 2012

(65) Prior Publication Data

US 2013/0062235 A1  Mar. 14, 2013

Related U.S. Application Data

(60) Provisional application No. 61/534,504, filed on Sep. 14, 2011.

(51) Int. Cl.

| | |
|---|---|
| *F16L 5/00* | (2006.01) |
| *B65D 85/24* | (2006.01) |
| *A61B 19/02* | (2006.01) |
| *A61L 2/26* | (2006.01) |
| *A61G 15/16* | (2006.01) |
| *A61B 17/00* | (2006.01) |
| *A61C 3/04* | (2006.01) |

(52) U.S. Cl.
CPC ............ *A61B 19/0256* (2013.01); *A61G 15/16* (2013.01); *A61L 2/26* (2013.01); *A61B 19/0271* (2013.01); *A61B 2017/00845* (2013.01); *A61B 2017/00862* (2013.01); *A61C 3/04* (2013.01); *A61L 2202/24* (2013.01); *Y10T 16/05* (2015.01); *Y10T 29/49947* (2015.01)

(58) Field of Classification Search
CPC ......................... H01R 13/5205; A61B 19/0256

USPC .............. 16/2.1–2.3; 206/339, 348, 363, 369, 206/438, 477, 482; 174/659, 660, 650; 248/346.04; 411/182, 339, 437, 510, 411/907

See application file for complete search history.

(56) References Cited

U.S. PATENT DOCUMENTS

| | | | |
|---|---|---|---|
| 2,438,499 A | | 3/1948 | Hartman |
| 2,664,458 A | | 12/1953 | Rapata |
| 3,110,337 A | | 11/1963 | Biesecker |
| 3,217,584 A | | 11/1965 | Amesbury |
| 3,245,428 A | * | 4/1966 | Klimak et al. ............ 174/153 G |
| 3,285,456 A | * | 11/1966 | Pewitt ................ A47G 23/0241 215/12.1 |
| 3,309,955 A | | 3/1967 | Turnbull et al. |
| 3,351,974 A | * | 11/1967 | Wilhelmi .......................... 16/2.1 |
| 3,516,111 A | * | 6/1970 | Heyman ........................... 16/2.1 |
| 3,611,861 A | | 10/1971 | Schulze |
| 3,651,734 A | | 3/1972 | McSherry |
| 3,678,797 A | | 7/1972 | Seckerson |

(Continued)

*Primary Examiner* — Luan K Bui
(74) *Attorney, Agent, or Firm* — Hayes Soloway PC

(57) ABSTRACT

A grommet device and method of using a grommet device is provided. The device includes a base structure having a base surface and a top structure having a top surface. A middle portion is connected between the top structure and the base structure, wherein an aperture is positioned through the middle portion, the aperture having an interior space defined by an aperture sidewall extending from the base surface to the top surface. A protruding structure is affixed to a portion of the aperture sidewall at a first end and extending towards a central axis of the aperture along a protrusion axis, wherein the protrusion axis is substantially aligned with a length of the protruding structure from the first end to the second end, and wherein a second end of the protruding structure is flexibly movable in at least one direction substantially perpendicular to the protrusion axis.

17 Claims, 6 Drawing Sheets

(56) References Cited

U.S. PATENT DOCUMENTS

| | | | |
|---|---|---|---|
| 3,964,364 A | 6/1976 | Poe | |
| 4,136,599 A | 1/1979 | Hammer, Jr. | |
| 4,276,806 A | 7/1981 | Morel | |
| 4,843,675 A | 7/1989 | Diamantis | |
| 5,518,115 A * | 5/1996 | Latulippe | 206/438 |
| 5,525,314 A * | 6/1996 | Hurson | 206/369 |
| 5,579,929 A * | 12/1996 | Schwartz | B01L 9/06 |
| | | | 206/446 |
| 5,645,282 A * | 7/1997 | Belter | 411/182 |
| 5,702,076 A * | 12/1997 | Humber | 248/57 |
| 5,775,859 A | 7/1998 | Anscher | |
| 5,954,345 A * | 9/1999 | Svoboda et al. | 16/2.3 |
| 5,975,820 A | 11/1999 | Kirchen | |
| 6,099,812 A | 8/2000 | Allen et al. | |
| 6,278,061 B1 * | 8/2001 | Daoud | 174/659 |
| 6,364,586 B1 | 4/2002 | Okada | |
| 6,382,575 B1 | 5/2002 | Frush et al. | |
| 6,505,386 B1 | 1/2003 | Allie | |
| 6,514,023 B2 | 2/2003 | Moerke | |
| 6,854,946 B2 | 2/2005 | Bauer | |
| 7,579,557 B2 * | 8/2009 | Tapper | 174/650 |
| 7,615,714 B2 * | 11/2009 | Pyron et al. | 174/660 |
| 2006/0261695 A1 | 11/2006 | Terrill et al. | |
| 2007/0138042 A1 | 6/2007 | Wood | |
| 2008/0166682 A1 | 7/2008 | Bjorn et al. | |
| 2010/0065456 A1 | 3/2010 | Junk et al. | |
| 2010/0261955 A1 | 10/2010 | O'Hern et al. | |
| 2011/0014005 A1 | 1/2011 | Shinozaki | |
| 2011/0091301 A1 | 4/2011 | Shimizu et al. | |
| 2011/0170982 A1 | 7/2011 | Watanabe | |
| 2011/0197405 A1 | 8/2011 | Kato et al. | |
| 2012/0159740 A1 * | 6/2012 | Strelow et al. | 16/2.2 |

* cited by examiner

UNIVERSALLY-SIZED GROMMET DEVICE AND METHOD THEREOF

CROSS REFERENCE TO RELATED APPLICATION

This application claims benefit of U.S. Provisional Application Ser. No. 61/534,504, entitled, "Universally-Sized Grommet Device and Method Thereof" filed Sep. 14, 2011, the entire disclosure of which is incorporated herein by reference.

FIELD OF THE DISCLOSURE

The present disclosure is generally related to grommets and more particularly is related to a universally-sized grommet device and method thereof.

BACKGROUND OF THE DISCLOSURE

Within the medical industry, there is a need for holding a variety of medical instruments for various purposes. For example, a surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. However, with smaller tools, such as small dental tools, it is frequently inefficient to store them in these containers, since they're prone to being moved around and jostled as the container is moved. This may result in a grouping of smaller tools in one area, which means that the surgeon or medical staff member must sift through the grouping to locate a specific tool.

Conventionally, medical instruments are often held in containers or trays with holes and grommets. The grommets may be positioned within the hole and provide a secure interface between the medical instrument and the hole within the container or tray. Often, the grommets are sized to match a certain shaft size of a medical instrument, and a container or tray may include a variety of different sized grommets, each specifically engineered and designed to hold one of a variety of medical instruments. These medical instruments have varying shaft sizes and it often becomes tedious to search for the appropriately sized grommet that matches a particular shaft size of the medical instrument. It is not uncommon for a medical tray to have fifty or more grommets, with a dozen or more different sizes. Thus, the time it takes to match a specific medical instrument to a specifically sized grommet may result in inefficient use valuable time.

Thus, a heretofore unaddressed need exists in the industry to address the aforementioned deficiencies and inadequacies.

SUMMARY OF THE DISCLOSURE

Embodiments of the present disclosure provide a grommet device. Briefly described, in architecture, one embodiment of the system, among others, can be implemented as follows. The grommet device includes a base structure having a base surface. A top structure has a top surface. A middle portion is connected between the top structure and the base structure, wherein an aperture is positioned through the middle portion, the aperture having an interior space defined by an aperture sidewall extending from the base surface to the top surface. A protruding structure is affixed to a portion of the aperture sidewall at a first end and extending towards a central axis of the aperture along a protrusion axis, wherein the protrusion axis is substantially aligned with a length of the protruding structure from the first end to a second end, and wherein the second end of the protruding structure is flexibly movable in at least one direction substantially perpendicular to the protrusion axis.

The present disclosure can also be viewed as providing a medical instrument holding device. Briefly described, in architecture, one embodiment of the device, among others, can be implemented as follows. A medical instrument sterilization tray has a plurality of holes formed therein. A grommet is positioned within one of the plurality of holes, the grommet device formed from a base structure having a base surface, a top structure having a top surface, a middle portion connected between the top structure and the base structure, wherein an aperture is positioned through the middle portion, the aperture having an interior space defined by an aperture sidewall extending from the base surface to the top surface, a protruding structure affixed to a portion of the aperture sidewall and positioned within the aperture, wherein the protruding structure extends along a protrusion axis to intersect a central axis of the aperture. A medical instrument is positioned within the aperture, wherein the protruding structure frictionally biases the medical instrument against the aperture sidewall in a direction substantially perpendicular to the protrusion axis.

The present disclosure can also be viewed as providing methods of securing a medical instrument with a grommet device. In this regard, one embodiment of such a method, among others, can be broadly summarized by the following steps: securing the grommet device within a hole of a grommet-holding structure, wherein the grommet device has a base structure with a base surface, a top structure with a top surface, and a middle portion connected between the top structure and the base structure, wherein an aperture is positioned through the middle portion; inserting at least a portion of the medical instrument within an interior space of an aperture positioned, wherein the interior space is defined by an aperture sidewall; biasing the inserted portion of the medical instrument towards a first portion of the aperture sidewall with a biased protruding structure, wherein the protruding structure is affixed to a second portion of the aperture sidewall; and retaining the medical instrument within the aperture with the biased protruding structure.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
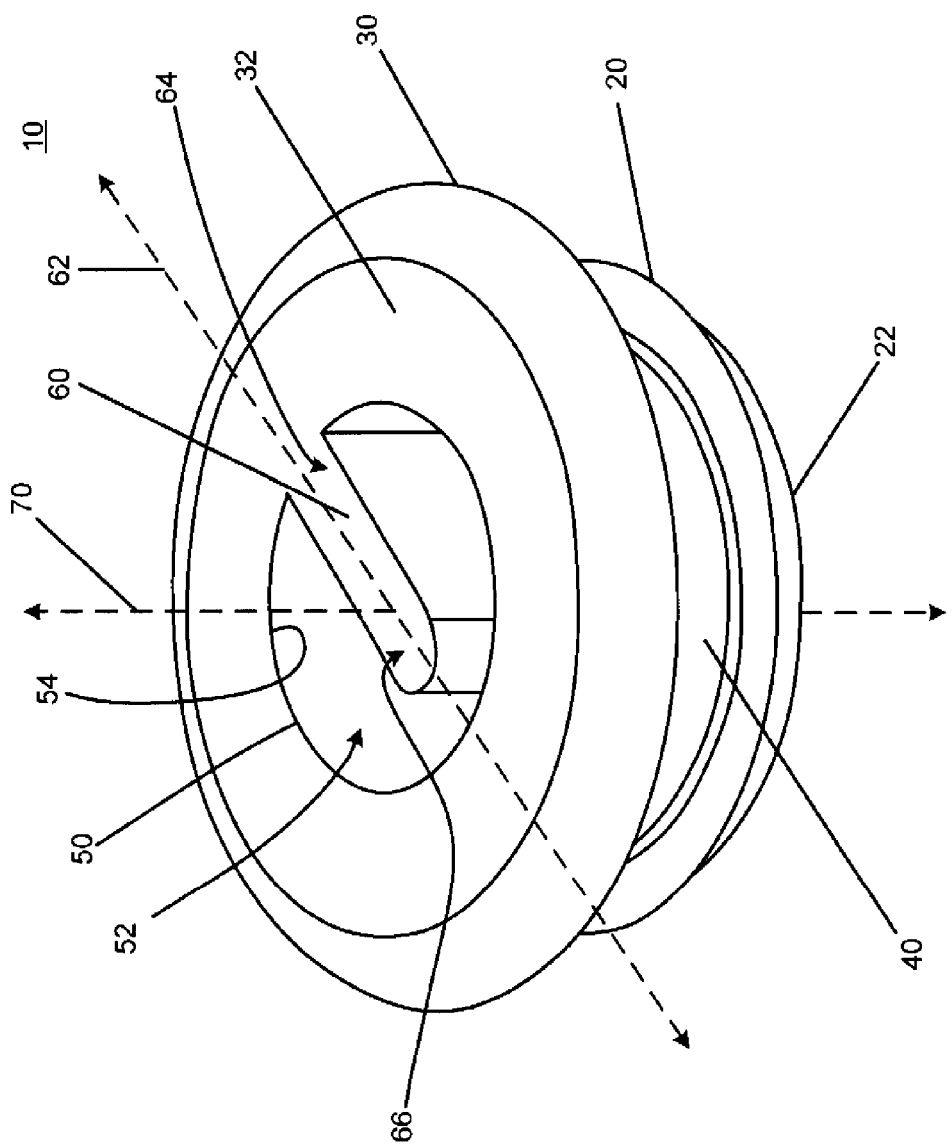
FIG. 1 is a plan view illustration of a grommet device, in accordance with a first exemplary embodiment of the present disclosure.

FIG. 1 is a plan view illustration of a grommet device 10, in accordance with a first exemplary embodiment of the present disclosure. The grommet device 10, which may be referred to as 'device 10,' includes a base structure 20 having a base surface 22 and a top structure 30 having a top surface 32. A middle portion 40 is connected between the top structure 30 and the base structure 20, wherein an aperture 50 is positioned through the middle portion 40. The aperture 50 has an interior space 52 defined by an aperture sidewall 54 extending from the base surface 22 to the top surface 32. A protruding structure 60 affixed to a portion of the aperture sidewall 54 at a first end 64 and extending towards a central axis 70 of the aperture 50 along a protrusion axis 62, wherein the protrusion axis 62 is substantially aligned with a length of the protruding structure 60 from the first end 64 to a second end 66, and wherein the second end 66 of the protruding structure 60 is flexibly movable in at least one direction substantially perpendicular to the protrusion axis 62.

The device 10 may be used with medical tool holding structures, such as sterilization trays used for holding medical instruments during a sterilization process. Accordingly, the device 10 may be used in any industry utilizing medical tools, such as tools, instruments, or any other type of implement used for surgical procedures, operations, or other medical procedures. For example, the device 10 may be used to hold medical instruments in surgical environments before, during and/or after a surgical procedure, or a medical instrument sterilization process. Similarly, the device 10 may be used with dental instruments for dental operations, routine cleanings, or for any other use. Other settings and uses within the medical field are also envisioned, all of which are considered within the scope of the present disclosure.

Figure 2:
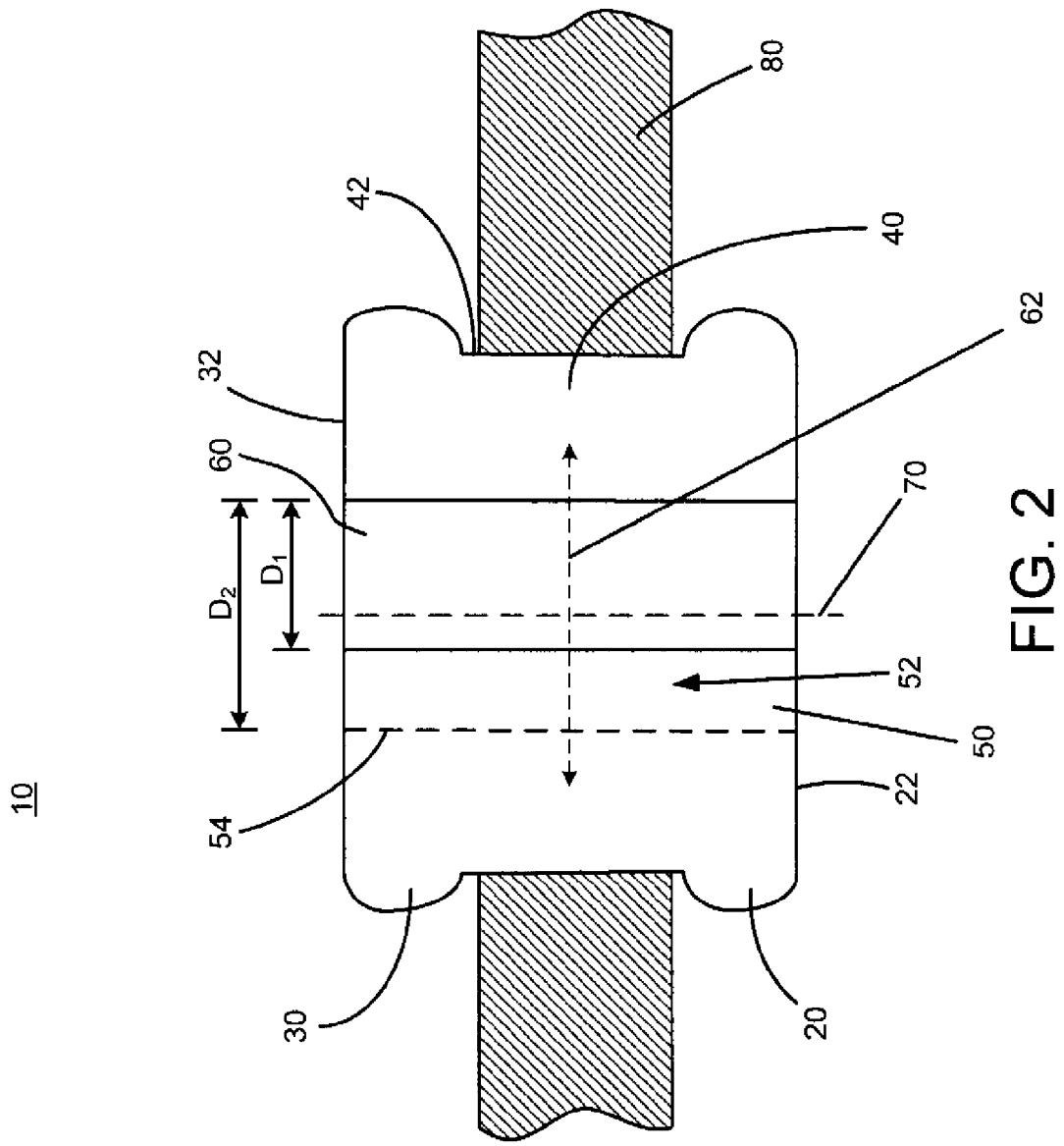
FIG. 2 is a cross-sectional view illustration of the grommet device, in accordance with the first exemplary embodiment of the present disclosure.

FIG. 2 is a cross-sectional view illustration of the grommet device 10, in accordance with the first exemplary embodiment of the present disclosure. As is shown in FIGS. 1-2, the base structure 20 of the device may be configured to be placed on one side of a grommet holding structure 80, which may be an opening, hole, or aperture within a medical sterilization tray or other, similar structure. The base structure 20 may be sized slightly larger than the grommet holding structure 80, thereby allowing the base structure 20 to be biased into position. For example, many sterilization trays include a plurality of holes for holding medical instruments. To secure the medical instrument properly during a medical sterilization process, the device 10 may be inserted into the hole by pushing the base structure 20 through the hole until the base structure 20 is located on one side of the tray, and the top structure is located on an opposing side of the tray. Accordingly, the hole may be the grommet-holding structure 80. In this position, the base surface 22 may be positioned interior of, or below the medical sterilization tray. In other words, the plane of the base surface 22 may be substantially parallel to the plane of the sterilization tray, but not co-planar to the plane of the sterilization tray.

The top structure 30 may be sized similar to the base structure 20, in that the top structure 30 is sized larger than the grommet-holding structure 80. This may prevent the device 10 from slipping or moving out of position within the grommet-holding structure 80. The top structure 30 may also be oriented such that the plane of the top surface 32 is substantially parallel to the plane of the sterilization tray or other structure that the grommet-holding structure 80 is positioned in, but not co-planar to the sterilization tray. Accordingly, the base and top structures 20, 30 may have any size exterior diameters, thicknesses, or other dimensions. Similarly, the overall dimensions of the device 10, including the overall thickness and external diameter may have any size.

The middle portion 40 may integrally connect the base structure 20 to the top structure 30. The middle portion 40 may commonly have a substantially cylindrical shape that is configured to be positioned within the grommet-holding structure 80. For example, as is shown in FIG. 2, the middle portion 40 may be positioned abutting the grommet-holding structure 80, whereby the base and top structures 20, 30 are positioned below and above the grommet-holding structure 80, respectively.

The aperture 50 may be positioned within the device 10, connecting the top surface 32 with the base surface 22. In other words, the aperture 50 is a cut-out of material, or hole, that is positioned within the device 10, commonly aligned along a central axis 70 of the cylindrical shape of the device 10. This central axis 70 may run through a center point of the grommet-holding structure 80, or may be positioned off-center, as various designs may dictate. The aperture 50 may be sized to hold any type of medical instrument, and thus, may have any size diameter. The aperture 50 includes an interior space 52, which may be defined by the aperture sidewall 54. The interior space 52 may be characterized as the space within the aperture 50 that is surrounded by the aperture sidewall 54.

The protruding structure 60 may be positioned along any portion of the aperture sidewall 54, such as connected to a particular region of the aperture sidewall 54, as is shown in FIG. 1. The protruding structure 60, which may be referred to as a 'rudder,' may be constructed from the same materials as the other components of the device 10, and may generally be integrally connected to at least one of the base structure 20, top structure 30, and middle portion 40. The protruding structure 60 may be sized and positioned to be located from the aperture sidewall 54 where it is connected, protruding towards the central axis 70 along the protrusion axis 62. The portion of the protruding structure 60 that protrudes towards the central axis 70, i.e., the mid-section of the protruding structure 60 and the second end 66, may be flexibly movable within the aperture 50, such that the protruding structure 60 is movable in a variety of directions within the aperture 50, namely laterally movable. In other words, the movement of the protruding structure 60 may be in directions that are substantially perpendicular to the protrusion axis 62.

Figure 3:
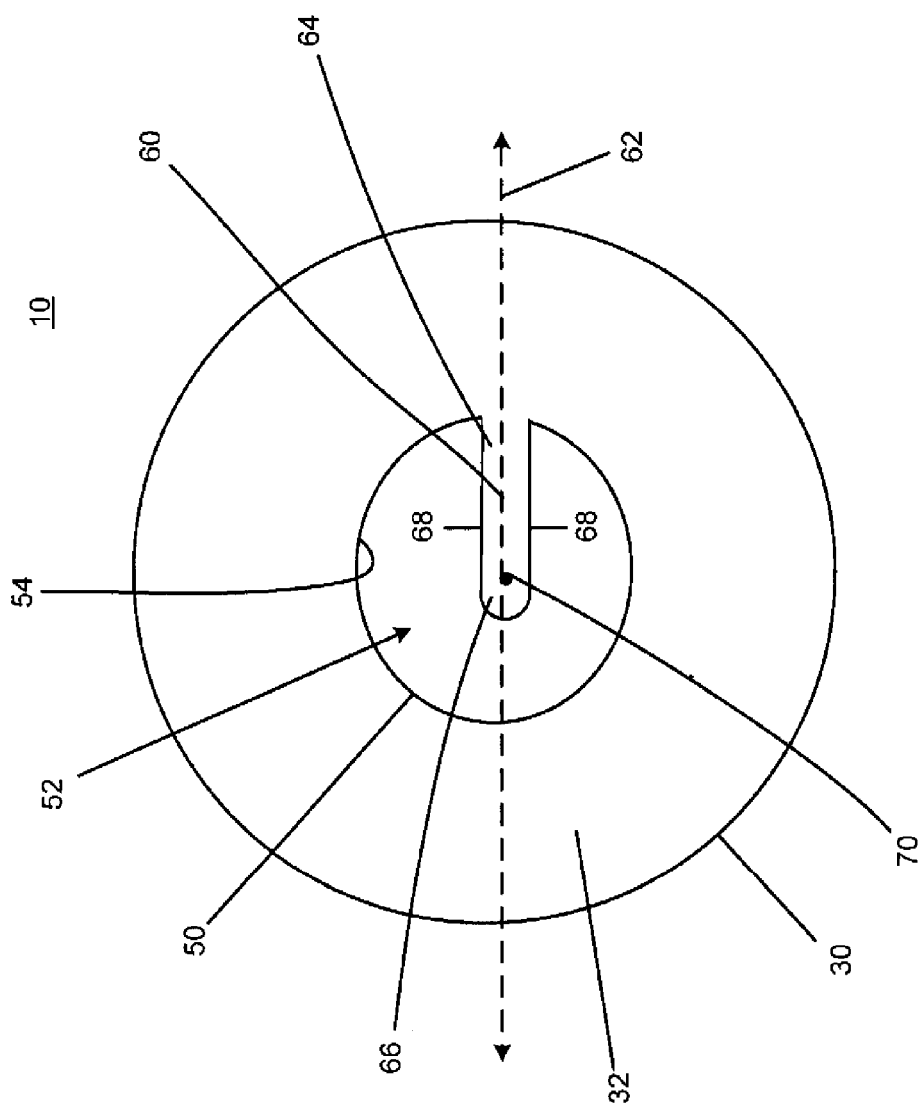
FIG. 3 is a top view illustration of the grommet device, in accordance with the first exemplary embodiment of the present disclosure.

The protruding structure 60 may have a natural position, i.e., a position of original manufacture. This natural position is shown in FIGS. 1-3 as substantially centered with in the aperture 60 and intersecting the central axis 70. When the protruding structure 60 is not being contacted or otherwise biased by a medical instrument, the protruding structure 60 will be located in its natural position. On the other hand, when the protruding structure 60 is contacted by a medical instrument, the end of the protruding structure 60 will be moved in a direction that is substantially perpendicular to the protrusion axis 62 and into one of a plurality of biased positions, i.e., any other position but the natural position.

Although the overall size of the protruding structure 60 may vary, depending on design, the protruding structure 60 may commonly be sized to intersect the central axis 70. In other words, the overall length, indicated as $D_1$ in FIG. 2, of the protruding structure 60 may include any length that is less than the diameter of the aperture 50, indicated as $D_2$ in FIG. 2. This may include a protruding structure 60 has a length dimension that is sized between ¼ to ¾ of that of the diameter of the aperture 50, $D_2$. It is noted that the protruding structure 60 may include a variety of shapes, sizes, textures, and features. For example, the edges of the protruding structure 60 may be chamfered or rounded. The surfaces of the protruding structure 60 may also have a given texture, such as a texture to increase friction and help retain a medical instrument.

The protruding structure 60 may be constructed such that it can be biased in a variety of directions. For example, when a medical instrument is inserted into the aperture 50, the protruding structure 60 may be biased towards the aperture sidewall 54 by the shaft of the medical instrument. When this occurs, the protruding structure 60 contacts the shaft of the medical instrument and biases towards an opposing portion of the aperture sidewall 54, since the protruding structure 60 has been manufactured to return to its natural position. This biasing force on the shaft of the medical instrument may retain the medical instrument within the aperture 50, and therefore, in a secure position in the device 10. Additionally, since the protruding structure 60 may be biased in varying degrees, the device 10 may accommodate a number of medical instruments with many different sized shafts. This ability allows the device 10 to be universal in its ability to properly retain a variety of medical instruments. Of course, medical instruments with shafts larger than the diameter $D_2$ of the aperture 50, or shafts small enough that they fail to bias the protruding structure 60 when inserted into the aperture 50, may not, in common situations, be used with the device 10 as described herein.

The device 10 may be a substantially cylindrical structure around the base structure 20, the top structure 30, the middle portion 40, and the protruding structure 60, all of which may be integrally connected. As is shown in FIG. 2, the middle portion 40 may have an engagement area 42 at an exterior surface of the middle portion 40 that engages or contacts the grommet-holding structure 80. The engagement area 42 may be formed between the edges of the top structure 30 and base structure 20 that abut the exterior surface of the middle portion 40. Commonly, the device 10 may be constructed from a rubber or silicon material that is substantially resistant to degradation from use and from sterilization environments. Within the medical industry, medical instruments are often sterilized in autoclaves, which utilize high temperatures, high pressures, moisture, and/or chemicals to sterilize a medical instrument.

FIG. 3 is a top view illustration of the grommet device 10, in accordance with the first exemplary embodiment of the present disclosure. As is shown, the protruding structure 60 may be integrally connected with the aperture sidewall 54 of the device and may be positioned to intersect the central axis 70 of the device 10. In this position, the end of the protruding structure 60, i.e., the part of the protruding structure 60 that is positioned near the central axis 70, may be capable of being biased towards one or another side of the central axis 70. Additionally, it is shown in FIG. 3 that the aperture 50 extends through the device 10, from the top surface 32 to the base surface 22 (FIG. 2).

As is shown in FIG. 3, the second end 66 of the protruding structure 60 may be a curved portion having an arc shape. The second end 66 is connected to the first end 64 with a middle section of the protruding structure 60, i.e., the section of the protruding structure 60 that is located between the first and second ends 64, 66. The middle section of the protruding structure 60 may have at least two substantially parallel walls 68. These two substantially parallel walls 68 may be positioned substantially parallel to the protrusion axis 62. The two substantially parallel walls 68 may be used to retain a medical instrument, as is discussed relative to FIG. 4.

Figure 4:
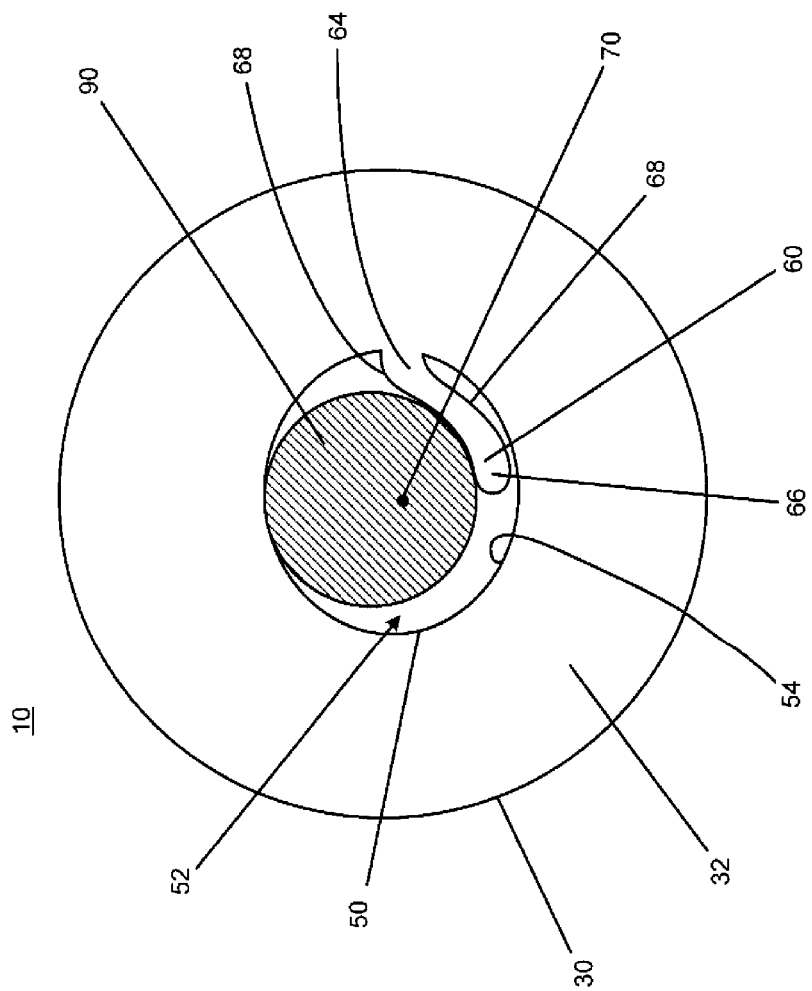
FIG. 4 is a top view illustration of the grommet device with a medical instrument shaft, in accordance with the first exemplary embodiment of the present disclosure.

FIG. 4 is a top view illustration of the grommet device 10 with a medical instrument shaft 90, in accordance with the first exemplary embodiment of the present disclosure. As can be seen in FIG. 4, a medical instrument shaft 90 of a medical instrument, such as a scalpel, or other tool, is shown in the inserted positioned within the device 10. In this position, the medical instrument shaft 90 biases the protruding structure 60 towards the aperture sidewall 54, and away from the central axis 70. The medical instrument shaft 90 may be frictionally retained between the aperture sidewall 54 and the protruding structure 60, and more specifically, the medical instrument shaft 90 may contact a portion of the aperture sidewall 54 and only one of the at least two substantially parallel walls 68 of the protruding structure 60. Due to the flexibility of the protruding structure 60, when the medical instrument shaft 90 is positioned within the aperture 50, the two substantially parallel walls 68 may be moved to a non-parallel position with the protrusion axis (FIG. 3).

The protruding structure 60 is designed to move towards its natural position of manufacture when biased or placed under a force. Thus, the propensity of the protruding structure 60 to move towards its natural position may force the medical instrument shaft 90 towards the aperture sidewall 54, thereby retaining the medical instrument shaft 90 in a secure position. Since the protruding structure 60 can be biased and moved in a variety of ways and to a variety of degrees, the protruding structure 60 can successfully retain a medical instrument having a variety of shaft 90 sizes.

Figure 5:
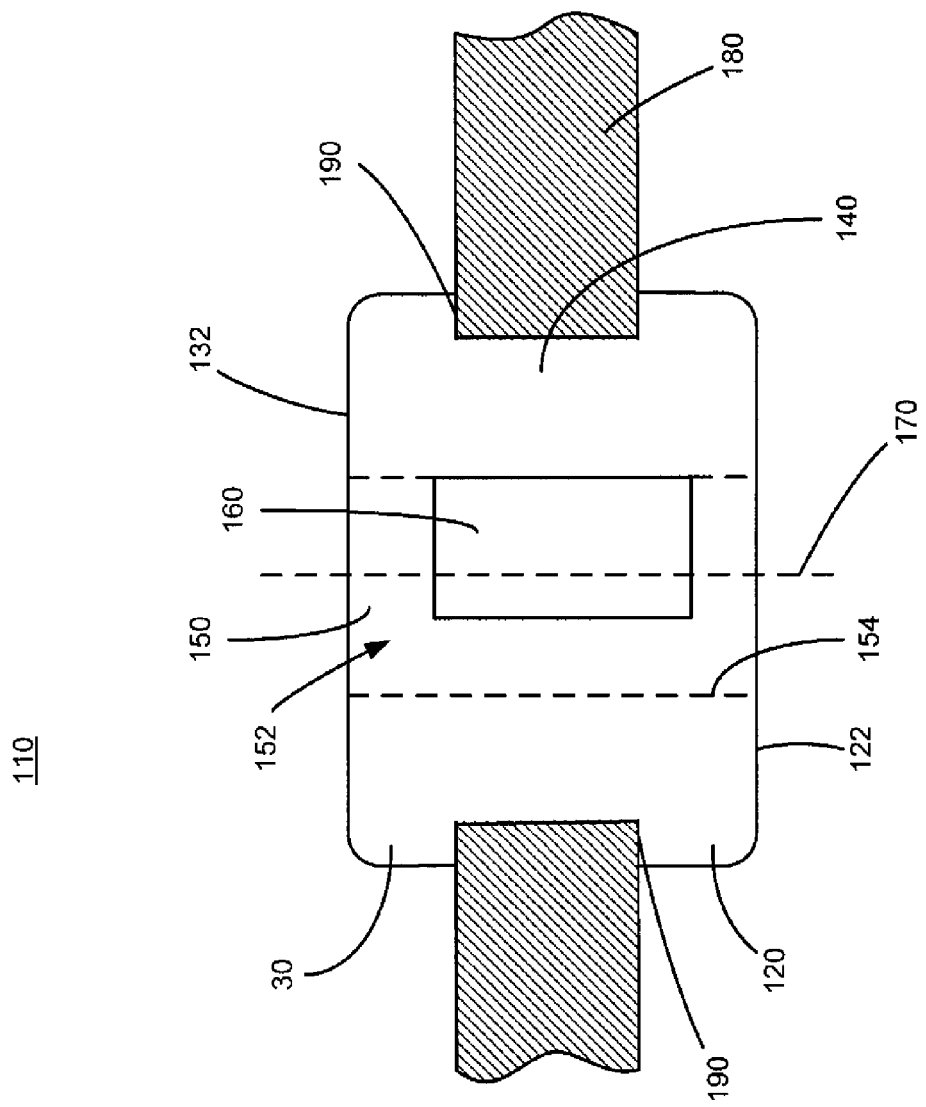
FIG. 5 is a cross-sectional view illustration of the grommet device, in accordance with a second exemplary embodiment of the present disclosure.

FIG. 5 is a cross-sectional view illustration of the grommet device 110, in accordance with a second exemplary embodiment of the present disclosure. The grommet device 110, which may be referred to as 'device 110,' may be substantially similar to the device 10 of the first exemplarily embodiment, and may include any of the components, features, or functions discussed with respect to the first exemplary embodiment. The device 110 includes a base structure 120 having a base surface 122 and a top structure 130 having a top surface 132. A middle portion 140 is connected between the top structure 130 and the base structure 120, wherein an aperture 150 is positioned through the middle portion 140. The aperture 150 has an interior space 152 defined by an aperture sidewall 154 extending from the base surface 122 to the top surface 132. A protruding structure 160 is affixed to a portion of the aperture sidewall 154 and is positioned within the aperture 150, wherein the protruding structure 160 extends towards a central axis 170 of the aperture 150.

As is shown in FIG. 5, the protruding structure 160 may be sized to have a smaller height than the overall device 110. In other words, the protruding structure 160 may be sized such that it is not flush with the top surface 132 and/or the base surface 122, or positioned between the top and base surfaces 132, 122. As one having skill in the art can see, the size and shape of the protruding structure 160 may include a variety of variations, all of which are considered within the scope of the present disclosure. Also shown in FIG. 5 is the seal 190 created between the grommet-holding device 180 and the device 110. The seal 190 is positioned between the grommet-holding device 180 and the exterior surface of the middle portion 140, and the edges of the top and base structures 130, 120. The purpose of the seal 190 is to prevent bacteria and other harmful contaminants from being located between the device 110 and the grommet-holding device 180, as these bacteria and contaminants may be detrimental to the sterilization of the device 110 and any medical tool carried therein. The seal 190 may be created by a tight tolerance and snug fit between the device 110 and the grommet-holding structure 180.

Figure 6:
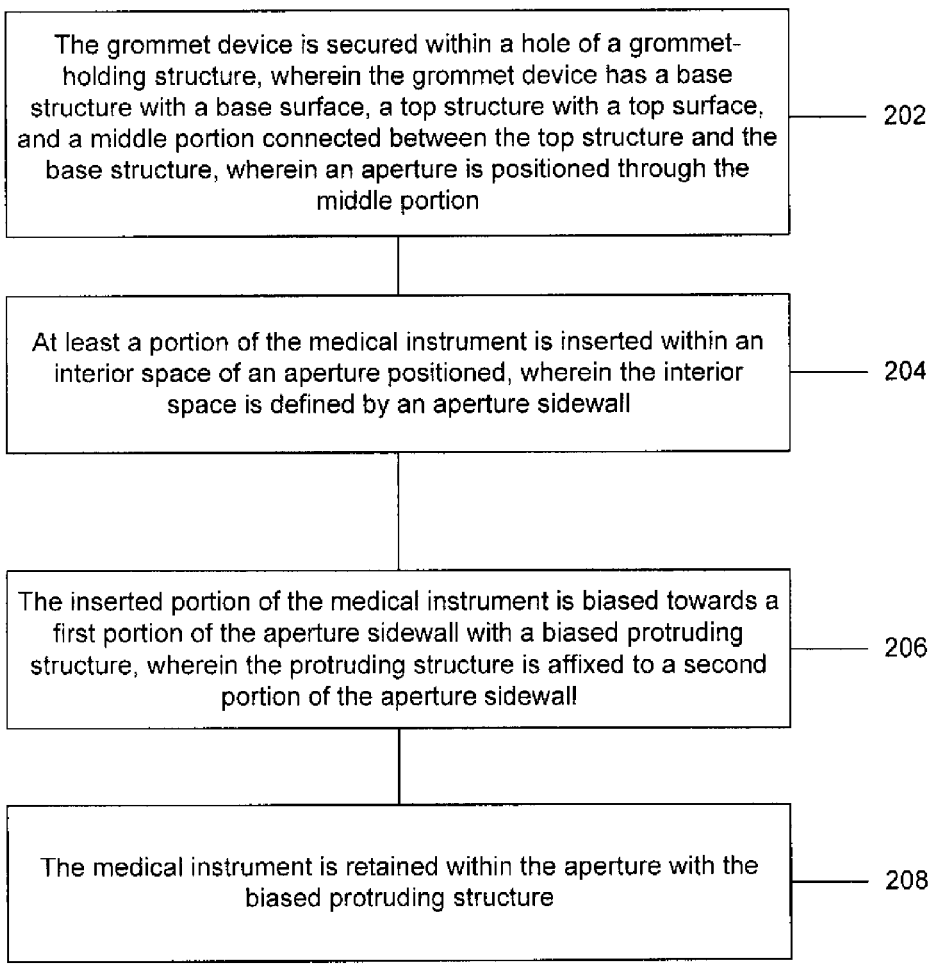
FIG. 6 is a flowchart illustrating a method of constructing a grommet device, in accordance with the first exemplary embodiment of the disclosure.

FIG. 6 is a flowchart 200 illustrating a method of securing a medical instrument with a grommet device 10, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, the grommet device is secured within a hole of a grommet-holding structure, wherein the grommet device has a base structure with a base surface, a top structure with a top surface, and a middle portion connected between the top structure and the base structure, wherein an aperture is positioned through the middle portion. At least a portion of the medical instrument is inserted within an interior space of an aperture positioned, wherein the interior space is defined by an aperture sidewall (block 204). The inserted portion of the medical instrument is biased towards a first portion of the aperture sidewall with a biased protruding structure, wherein the protruding structure is affixed to a second portion of the aperture sidewall (block 206). The medical instrument is retained within the aperture with the biased protruding structure (block 208).

The method may include a number of additional steps or variations thereof, including any of the steps, processes, or functions disclosed herein. For example, to sterilize a medical instrument, the grommet-holding structure, the grommet device, and the medical instrument may be subjected to a sterilization process while the medical instrument is retained within the aperture with the biased protruding structure. To secure the medical instrument within the grommet, the shaft of the medical instrument may be frictionally contacted between the aperture sidewall and the protruding structure. Once the sterilization process is complete, the medical instrument may be removed from the aperture, thereby allowing the biased protruding structure to move into a natural position. A seal may be created between an exterior surface of the middle portion and the grommet-holding structure to prevent harmful bacteria from contaminating crevices and small openings between the grommet and the grommet-holding structure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claim.

What is claimed is:

1. A grommet device comprising:
   a base structure having a base surface;
   a top structure having a top surface;
   a middle portion connected between the top structure and the base structure, wherein an aperture is positioned through the middle portion, the aperture having a central axis and having an interior space defined by an aperture sidewall extending from the base surface to the top surface; and
   a protruding structure affixed to a portion of the aperture sidewall at a first end and extending towards the central axis of the aperture along a protrusion axis, wherein the aperture is free from additional protruding structures, wherein the protruding structure intersects the central axis of the aperture, wherein the protrusion axis is substantially aligned with a length of the protruding structure from the first end to a second end, and wherein the second end of the protruding structure is flexibly movable in at least one direction that is both substantially perpendicular to the protrusion axis and substantially perpendicular to the central axis.

2. The grommet device of claim 1, wherein the flexibly movable second end of the protruding structure has a natural position and a plurality of biased positions, wherein the protruding structure intersects the central axis of the aperture in the natural position.

3. The grommet device of claim 2, wherein the flexibly movable second end of the protruding structure is located in one of the plurality of biased positions when it is contacted by a medical instrument, and wherein the flexibly movable second end of the protruding structure is located in the natural position when it is not contacted by the medical instrument.

4. The grommet device of claim 1, wherein the protruding structure extends from the base surface to the top surface.

5. The grommet device of claim 1, wherein wherein the second end of the protruding structure is connected to the first end with a middle section having at least two substantially parallel walls connected with a curved portion to form a continuous surface, wherein the at least two substantially parallel walls are substantially parallel to the protrusion axis.

6. A grommet device comprising:
   a base structure having a base surface;
   a top structure having a top surface;
   a middle portion connected between the top structure and the base structure, wherein an aperture is positioned through the middle portion, the aperture having a central and having an interior space defined by an aperture sidewall extending from the base surface to the top surface; and
   a protruding structure affixed to a portion of the aperture sidewall at a first end and extending towards the central axis of the aperture along a protrusion axis, wherein the aperture is free from additional protruding structures, wherein the protruding structure intersects the central axis of the aperture, wherein the protrusion axis is substantially aligned with a length of the protruding structure from the first end to a second end, and wherein the second end of the protruding structure is flexibly movable in at least one direction substantially perpendicular to the protrusion axis; and
   a medical instrument positioned within the aperture and frictionally retained between the aperture sidewall and the protruding structure, wherein the medical instrument contacts a portion of the aperture sidewall and only one of the at least two substantially parallel walls of the protruding structure.

7. The grommet device of claim 1, further comprising a sterilization tray engagement area located about an exterior of the middle portion, wherein the tray engagement area is abutted by an edge portion of the base structure and an edge portion of the top structure.

8. The grommet device of claim 1, wherein the protruding structure further comprises a length dimension that is sized between ¼ to ¾ of a diameter measurement of the aperture.

9. The grommet device of claim 1, wherein the protruding structure is constructed from at least one of: a rubber material, and a silicone material.

10. A grommet device comprising:
   a base structure having a base surface;
   a top structure having a top surface;
   a middle portion connected between the top structure and the base structure, wherein an aperture is positioned through the middle portion, the aperture having a central axis and having an interior space defined by an aperture sidewall extending from the base surface to the top surface; and
   a single protruding structure affixed to a portion of the aperture sidewall at a first end and extending towards the central axis of the aperture along a protrusion axis, wherein the aperture is free from additional protruding structures, wherein the protruding structure intersects the central axis of the aperture, wherein the protrusion axis is substantially aligned with a length of the protruding structure from the first end to a second end, and wherein the second end of the protruding structure is flexibly movable in at least one direction that is both substantially perpendicular to the protrusion axis and substantially perpendicular to the central axis.

11. The grommet device of claim 10, wherein the flexibly movable second end of the protruding structure has a natural position and a plurality of biased positions, wherein the protruding structure intersects the central axis of the aperture in the natural position.

12. The grommet device of claim 11, wherein the flexibly movable second end of the protruding structure is located in one of the plurality of biased positions when it is contacted by a medical instrument, and wherein the flexibly movable second end of the protruding structure is located in the natural position when it is not contacted by the medical instrument.

13. The grommet device of claim 10, wherein the protruding structure extends from the base surface to the top surface.

14. The grommet device of claim 10, wherein the second end of the protruding structure is connected to the first end with a middle section having at least two substantially parallel walls connected with a curved portion to form a continuous surface, wherein the at least two substantially parallel walls are substantially parallel to the protrusion axis.

15. The grommet device of claim 10, further comprising a sterilization tray engagement area located about an exterior of the middle portion, wherein the tray engagement area is abutted by an edge portion of the base structure and an edge portion of the top structure.

16. The grommet device of claim 10, wherein the protruding structure further comprises a length dimension that is sized between ¼ to ¾ of a diameter measurement of the aperture.

17. The grommet device of claim 10, wherein the protruding structure is constructed from at least one of a rubber material, and a silicone material.

* * * * *